US008663308B2

(12) United States Patent
Schafer et al.

(10) Patent No.: US 8,663,308 B2
(45) Date of Patent: Mar. 4, 2014

(54) GRAFT WITH BIOABSORBABLE SUPPORT FRAME

(75) Inventors: Michael Schafer, Bloomington, IN (US); Andrew W. Conder, Bloomington, IN (US); Robert W. Harrell, Indianapolis, IN (US); Marck Wassmann, Copenhagen (DK); Gert P. Andersen, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1791 days.

(21) Appl. No.: 11/522,835

(22) Filed: Sep. 18, 2006

(65) Prior Publication Data

US 2010/0262221 A1    Oct. 14, 2010

Related U.S. Application Data

(60) Provisional application No. 60/718,567, filed on Sep. 19, 2005.

(51) Int. Cl.
  *A61F 2/06* (2013.01)
(52) U.S. Cl.
  USPC ........................................................ 623/1.13
(58) Field of Classification Search
  USPC ........... 623/1.13, 1.14, 1.23, 1.25, 1.36, 1.11, 623/1.12, 1.15, 1.16, 1.17, 1.18, 1.19, 1.44, 623/1.45, 1.46, 1.47, 1.48; 606/191, 194, 606/198
  See application file for complete search history.

(56) References Cited

U.S. PATENT DOCUMENTS

| 4,116,731 | A | | 9/1978 | Tikhova et al. |
| 5,246,445 | A | * | 9/1993 | Yachia et al. ................... 623/1.2 |
| 5,693,085 | A | | 12/1997 | Buirge et al. |
| 5,873,904 | A | * | 2/1999 | Ragheb et al. ............... 623/1.13 |
| 6,206,931 | B1 | | 3/2001 | Cook et al. |
| 6,287,332 | B1 | | 9/2001 | Bolz et al. |
| 6,312,457 | B1 | * | 11/2001 | DiMatteo et al. ............ 623/1.13 |
| 6,395,208 | B1 | | 5/2002 | Herweck et al. |
| 6,544,357 | B1 | | 4/2003 | Hehmann et al. |
| 2002/0004060 | A1 | | 1/2002 | Heublein et al. |

(Continued)

FOREIGN PATENT DOCUMENTS

| WO | WO 97/24081 A1 | 7/1997 |
| WO | WO 99/03515 A2 | 1/1999 |

(Continued)

OTHER PUBLICATIONS

Atrium, "iCast™ Covered Stent for the treatment of tracheobronchial strictures," http://www.atriummed.com/Products/Interventional/icast.asp Aug. 24, 2005.

(Continued)

*Primary Examiner* — Ryan Severson
*Assistant Examiner* — Jonathan W Miles
(74) *Attorney, Agent, or Firm* — Brinks Gilson & Lione

(57) ABSTRACT

The medical devices, such as stent grafts, described herein preferably include a tubular remodelable graft material attached to a support frame formed at least in part from a metallic bioabsorbable material. The remodelable graft material preferably includes an extracellular matrix material such as small intestinal submucosa (SIS). The support frame attached to the graft is preferably a bioabsorbable magnesium alloy. The devices may be implanted within a peripheral vascular body vessel from a percutaneous delivery catheter.

18 Claims, 4 Drawing Sheets

(56) References Cited

U.S. PATENT DOCUMENTS

| | | | |
|---|---|---|---|
| 2002/0165601 A1 | 11/2002 | Clerc | |
| 2002/0183716 A1 | 12/2002 | Herweck et al. | |
| 2004/0034409 A1 | 2/2004 | Heublein et al. | |
| 2004/0073297 A1 | 4/2004 | Rohde et al. | |
| 2004/0098095 A1 | 5/2004 | Burnside et al. | |
| 2004/0098108 A1 | 5/2004 | Harder et al. | |
| 2004/0172123 A1 | 9/2004 | Lootz et al. | |
| 2005/0071016 A1 | 3/2005 | Hausdorf et al. | |
| 2005/0079088 A1 | 4/2005 | Wirth et al. | |
| 2005/0131519 A1 | 6/2005 | Hartley | |
| 2005/0149167 A1 | 7/2005 | Osborne et al. | |
| 2005/0159804 A1 | 7/2005 | Lad et al. | |
| 2005/0266041 A1 | 12/2005 | Gerold et al. | |
| 2005/0273155 A1* | 12/2005 | Bahler et al. | 623/1.13 |
| 2006/0064160 A1 | 3/2006 | Gerold et al. | |
| 2007/0050009 A1* | 3/2007 | Flanagan | 623/1.15 |

FOREIGN PATENT DOCUMENTS

| | | |
|---|---|---|
| WO | WO 03/092471 A2 | 11/2003 |
| WO | WO 2004/022107 A2 | 3/2004 |
| WO | WO 2004/043474 A2 | 5/2004 |

OTHER PUBLICATIONS

Bard Peripheral Vascular, "Fluency® Tracheobronchial Stent Graft," http://www.bardpv.com/prod-fluency.php Aug. 24, 2005.

Antonio Colombo, MD; Evangelia Karvouni, MD, "Biodegradable Stents 'Fulfilling the Mission and Stepping Away'," *Circluation*, 2000; 102: 371-373.

L. Duffy, "Magnesium Alloys—Zirconium Containing Casting Alloys," http://www.azom.com/details.asp?ArticleID=359.

Magnesium Elektron, "Elektron WE-43 Wrought Alloy," Datasheet: 478.

Magnesium Elektron, "Elektron WE-43 Wrought Alloy," Datasheet: 467.

B. Heublein, R. Rohde, V. Kaese, M. Niemeyer, W. Hartung, A. Haverich, "Biocorrosion of magnesium alloys: a new principle in cardiovascular implant technology?" www.heartjnl.com 2003: 89:651-656.

Jostent® Coronary Stent Graft, "Summary of Safety and Probable Benefit," JOMED AB, Sweden, Oct. 26, 1999.

Mazur A., Maier JA, Rock E, Gueux E, Nowacki W. Rayssiguier Y, "Magnesium and the inflammatory response: Potential physiopathological implications," *Arch Biochem Biophys*. Apr. 19, 2006.

Dennis Salzman, Ph.D, "FLUENCY® Plus Tracheobronchial Stent Graft 510(k) Summary of Safety and Effectiveness 21 CFR 807. 92(a)" Bard Peripheral Vascular, Inc.

Hideo Tamai, Keiji Igaki, Eisho Kyo, Kunihiko Kosuga, Akiyoshi Kawashima, Shigeo Matsui, Hidenori Komori, Takafumi Tsuji, Seiichiro Motohara and Hiromu Uehata, "Initial and 6-Month Results of Biodegradable Poly-l-Lactic Acid Coronary Stents in Humans," *Circulation* 2000; 102:399-404.

Ron Waksman, MD, Facc, Rjbabu Pakala, PhD, Pramod K. Kuchulakanti, MD, Richard Baffour, PhD, David Hellinga, MSc, Rufus Seabron, Fermin O. Tio, MD, Eric Wittchow, PhD, Sonja Hartwig PhD, Claus Harder, PhD, Roland Rohde, MD, Bernd Heublein, MD, Arnim Andreae DVM, Karl-Heinz Waldmann, MD, Axel Haverich, MD, "Safety and efficacy of bioabsorbable magnesium alloy stents in porcine coronary arteries," http://www3.interscience.wiley.com/cgi-bin/fulltext/112782886/main.html,journal-article.

* cited by examiner

GRAFT WITH BIOABSORBABLE SUPPORT FRAME

RELATED APPLICATIONS

This application claims priority to U.S. Provisional Patent Application No. 60/718,567, entitled "Bioabsorbable Support Frame Graft," filed Sep. 19, 2005, which is incorporated herein by reference in its entirety.

TECHNICAL FIELD

The present invention relates to medical devices for implantation in a body vessel. More particularly, the present invention relates to implantable medical device frames comprising a bioabsorbable material.

BACKGROUND

Various implantable medical devices and minimally-invasive methods of transcatheter implantation of these devices have been developed to deliver medical devices within the lumen of a body vessel. These devices are advantageously inserted intravascularly, for example from an implantation catheter. Implantable medical devices can function as a stent to hold open an occluded or narrowed body vessel. Such devices can comprise an expandable frame configured for implantation in the lumen of a body vessel and a graft material attached to the frame. Various conditions, such as peripheral vascular disease and creation or reinforcement of hemodialysis fistulas, can be ameliorated by implantation of a medical device within a body vessel to provide a stenting function therein.

Peripheral vascular disease (PVD) is a condition with variable morbidity affecting mostly men and women older than 50 years. Peripheral vascular disease of the lower extremities may cause a variety of clinical indications from asymptomatic patients to patients with chronic critical limb ischemia (CLI) that might result in amputation and limb loss. Critical limb ischemia may impair the patient functional status and quality of life, and may be associated with an increased cardiovascular mortality and morbidity. Critical limb ischemia may be a chronic condition accompanied by acute conditions such as distal embolization, external compression, or acute thrombosis. Based on incidence rates extrapolated to today's increasingly aging population, PVD may affect as many as 10 million people in the United States (Becker G J, McClenny T E, Kovacs M E, et al., "The importance of increasing public and physician awareness of peripheral arterial disease," *J Vasc Interv Radiol.*, 13(1):7-11 (January 2002)). As the population ages, the family physician may be faced with increasing numbers of patients complaining of symptoms of lower extremity PVD. Nearly one in four of the approximately 60,000 people screened annually through Legs for Life, a nationwide screening program, are believed to be at moderate to high risk of lower extremity PVD and are referred to their primary care physicians for diagnosis (data collected by the Society of Cardiovascular and Interventional Radiology) (Becker G J, McClenny T E, Kovacs M E, et al., "The importance of increasing public and physician awareness of peripheral arterial disease," *J Vasc Interv Radiol.*, 13(1):7-11 (January 2002)).

Chronic critical limb ischemia may be defined not only by the clinical symptoms, but also by an objective measurement of impaired blood flow. Criteria for diagnosis include either one of the following: (1) more than two weeks of recurrent foot pain at rest that requires regular use of analgesics and is associated with an ankle systolic pressure of 50 mm Hg or less, or a toe systolic pressure of 30 mm Hg or less, or (2) a nonhealing wound or gangrene of the foot or toes, with similar hemodynamic measurements. The hemodynamic parameters may be less reliable in patients with diabetes because arterial wall calcification can impair compression by a blood pressure cuff and produce systolic pressure measurements that are greater than the actual levels. Ischemic rest pain is classically described as a burning pain in the ball of the foot and toes that is worse at night when the patient is in bed. The pain is exacerbated by the recumbent position because of the loss of gravity-assisted flow to the foot. Ischemic rest pain is located in the foot, where tissue is farthest from the heart and distal to the arterial occlusions. Patients with ischemic rest pain often need to dangle their legs over the side of the bed or sleep in a recliner to regain gravity-augmented blood flow and relieve the pain. Patients who keep their legs in a dependent position for comfort often present with considerable edema of the feet and ankles. Nonhealing wounds are usually found in areas of foot trauma caused by improperly fitting shoes or an injury. A wound is generally considered to be nonhealing if it fails to respond to a four- to 12-week trial of conservative therapy such as regular dressing changes, avoidance of trauma, treatment of infection and débridement of necrotic tissue. Gangrene may be found on the toes, occurring when the blood supply is so low that spontaneous necrosis occurs in the most poorly perfused tissues.

Treatment and prognosis of peripheral vascular disease can be influenced by lesion and patient characteristics, such as the site of the lesion, type of lesion (stenosis or occlusion, lesion length), arterial runoff, and clinical manifestation (Dormandy J A, Rutherford R B., "Management of peripheral arterial disease (PAD): TASC Working Group," *J Vasc Surg*, 31(1 pt 2):S103-S106 (2000)). Estimates of the 5-year patency rate of balloon dilation for femoropopliteal arterial disease range from as low as 12% in patients with an occlusion and critical ischemia to 68% in patients with a stenosis and claudication (Hunink M G M, Wong J B, Donaldson M C, Meyerovitz M F, Harrington D P., "Patency results of percutaneous and surgical revascularization for femoropopliteal arterial disease," *Med Decis Making*, 14:71-81 (1994)). Bypass surgery for femoropopliteal arterial disease has been associated not only with higher long-term patency rates but also with a higher procedural morbidity, mortality, and a longer hospital stay (Hunink M G M, Wong J B, Donaldson M C, Meyerovitz M F, de Vries J A, Harrington D P., "Revascularization for femoropopliteal disease, A decision and cost-effectiveness analysis," *Journal of the American Medical Assoc.*, 274:165-171 (1995)).

Implantable medical devices comprising an implantable frame and attached graft material may also be configured to provide for the creation or the repair of hemodialysis fistulas. Patients with chronic renal failure can require regular hemodialysis. These patients often have a vascular access graft surgically placed in the arm to provide a high flow site for dialysis. Over time, the accesses can narrow and block off (occlude) due to buildup of intimal hyperplasia (scar tissue). Failing or occluded dialysis access grafts can cause morbidity, discomfort, or inconvenience for dialysis patients due to the need for invasive procedures to reestablish access flow, or to graft abandonment and reoperation. When failure occurs, per National Kidney Foundation Guidelines, an interventional radiologist normally performs a balloon angioplasty to reopen the fistula and regain access for dialysis. Many patients who are not candidates for renal transplantation or those for whom a compatible donor cannot be secured may be dependent on hemodialysis for their lifetime. This situation may result in the long-term need for and use of the dialysis access. Preservation of patent well-functioning dialysis fistulas is a challenging clinical problem in the long-term treatment of patients undergoing dialysis. Hospital admissions in the dialysis population have been attributed to vascular access problems, including fistula malfunction and thrombosis.

Native fistula or graft malfunction and thrombosis can be treated by using surgical thrombectomy and revision, or percutaneous techniques such as balloon angioplasty (percutaneous transluminal angioplasty [PTA]), thrombolysis, and mechanical thrombectomy. Implantation of medical devices configured as implantable stent grafts can prolong the patency of the vascular access and decreasing the morbidity and mortality of patients with chronic renal failure.

Various implantable medical devices can be endovascularly inserted within various body vessels from an implantation catheter. Minimally invasive techniques and instruments for placement of intraluminal medical devices have been developed to treat and repair such undesirable conditions within body vessels. Intraluminal medical devices can be introduced to a point of treatment within a body vessel using a delivery catheter device passed through the blood vessels communicating between a remote introductory location and the implantation site, and released from the delivery catheter device at the point of treatment within the body vessel. Intraluminal medical devices can be deployed in a vessel at a point of treatment, the delivery device withdrawn from the vessel, and the medical device retained within the vessel to provide sustained improvement in vascular function or to increase vessel patency. However, the implantation of medical devices within blood vessels can be complicated by incidence of inflammation or thrombus formation in the blood vessel proximate the site of implantation. Heightened incidence of inflammatory response may accompany implantation of frames that remain within a body vessel, such as a metallic or biostable stent. Thrombus formation on the implanted medical device can result in compromised medical device function, or other medical complications.

The formation of blood clots, or thrombus, on the surface of an endovascular prosthesis can both degrade the intended performance of the prosthesis and even undesirably restrict or occlude desirable fluid flow within a body vessel. Inhibiting or preventing thrombosis and platelet deposition on an implantable device within the body is important in promoting continued function of the medical device within the body, particularly within blood vessels. Post-implantation thrombosis and platelet deposition on surfaces of implantable medical devices prosthesis may undesirably reduce the patency rate of many implantable medical devices. For example, thrombosis and platelet deposition within an endovascular stent graft may occlude the conduit defined by the endovascular prosthesis. Many factors may contribute to thrombosis and platelet deposition on the surfaces of implanted prosthesis. The properties of the material or materials forming the endovascular prosthesis are believed to be one important factor that can contribute to the likelihood of undesirable levels of post-implantation thrombus formation or platelet deposition on the implanted device.

Implantable medical, or portions thereof, can advantageously comprise a bioabsorbable material for some applications. When an implanted medical device is only medically required for a limited period of time, medical devices can be designed to dissipate within the body vessel after the desired time period, typically on the order of up to about three months. Including a bioabsorbable material in the can allow for the decomposition or absorption of all or part of the support frame during a period subsequent to implantation in a body vessel. A bioabsorbable support frame can be used, for example, to avoid future surgical extraction of an implant that serves a temporary function or to provide a medical device with post-implantation properties, such as frame stiffness, that change with time as portions of the frame are absorbed. Medical devices formed from biodegradable polymers, such as poly(lactic acid) and the like, have been implanted to provide implantable frames that dissipate within a blood vessel after two to three months. However, intravascular implantation biodegradable polymer frames has been linked to undesirably high incidence of thrombus formation (T. Susawa et al., "Biodegradable intracoronary stents in adult dogs," *J. Am. Coll. Cardiol.,* 21:483 A (1993) and what has been characterized as a "significant inflammatory response" (A. Colombo et al., "Biodegradable Stents, 'Fulfilling the Mission and Stepping Away,'" *Circulation* 102:371-373 (2000)). Biodegradable polymeric stents may also have a resistance to radial compression that is greater than metallic stents, which may irritate body vessels that are prone to frequent collapse or dynamic movement. The peripheral blood vessels, such as the femoral, popliteal or illiac arteries, may be subject to dynamic movement during blood flow and body movement.

Recently, metal materials have been developed that are bioabsorbable while still providing some of the advantages of mechanical durability provided by metal support frames. For example, U.S. Pat. No. 6,287,332 (Bolz et al) and published U.S. Patent Application Nos. US 2005/0266041A1 (Gerold et. al.), US 2004/0098108 A1 (Harder et al.), US 2002/0004060 A1 (Heublein et al.), US 2005/0079088 A1 (Wirth et al.), US 2006/0064160 A1 (Gerold et al.) and US 2004/0098108A1 (Harder et al.) disclose medical devices formed from various metal materials that are absorbed upon implantation in a body vessel, particularly in coronary arteries. Many of these medical devices are bioabsorbable coronary stents comprising magnesium alloys.

The implantation of bioabsorbable magnesium alloy can provide a hypothrombogenic material with desired levels of radial flexibility. Stents in porcine coronary arteries have been reported by Waksman et al., "Safety and efficacy of bioabsorbable magnesium alloy stents in porcine coronary arteries," Catheter Cardiovasc Interv. Sep. 12, 2006 [Epub ahead of print; PubMED PMID: 16969879]. Magnesium is believed to play a role in cellular events involved in inflammation and thrombosis. For example, Mazur et al. recently reported that increases in extracellular magnesium concentration have been linked to decreases in inflammatory response (Mazur et al., "Magnesium and the inflammatory response: Potential physiopathological implications," Arch Biochem Biophys. Apr. 19, 2006; [Epub ahead of print; PubMED PMID: 16712775]), and "a direct role of low magnesium in promoting endothelial dysfunction by generating a pro-inflammatory, pro-thrombotic and pro-atherogenic environment . . . ." (Mazur, et al., "Low magnesium promotes endothelial cell dysfunction: implications for atherosclerosis, inflammation and thrombosis," *Biochem. Biophys. ACTA,* 1689(1): 13-21, May 24, 2004). In addition, in another report, Toft et al. found that "[m]agnesium has been shown to reduce platelet aggregation both in vitro and ex vivo, and this antiplatelet effect may be advantageous in the prevention of arterial thrombosis" (G. Toft, et al., "Intravenously and topically applied magnesium in the prevention of arterial thrombosis," *Thromb Res.* 99(1):61-9 (Jul. 1, 2000)).

For some medical applications, implantation of a stent graft may be advantageous. A stent graft typically includes a frame and a graft material attached to the frame. The frame may be sinusoidal hoop member attached to a tubular graft material. Typically, stent grafts are formed from metallic frame members comprising a plurality of struts and bends, attached to a tubular flexible material to define a tubular fluid conduit. For treatment of many conditions, it is desirable that graft material comprise remodelable material, permitting tissue ingrowth and absorption of the graft material within the body vessel over time. Implanted remodelable material provides a matrix or support for the growth of new tissue thereon, and remodelable material is resorbed into the body in which the device is implanted. Common events during this remodeling process include: widespread neovascularization, proliferation of granulation mesenchymal cells, biodegradation/resorption of implanted remodelable material, and absence of immune rejection. By this process, autologous cells from the body can replace the remodelable portions of the medical device. A variety of remodelable materials are available for use in implantable medical devices. Naturally derived or synthetic collagenous materials can be used to provide remodelable surfaces on implantable medical devices. Naturally derived or synthetic collagenous material, such as extracellular matrix material, are another category of remodelable materials that include, for instance, submucosa, renal capsule membrane, dura mater, pericardium, serosa, and peritoneum or basement membrane materials. One specific example of an extracellular matrix material is small intestine submucosa (SIS). When implanted, SIS can undergo remodeling and can induce the growth of endogenous tissues upon implantation into a host.

What are needed for some medical applications are medical devices having a support frame comprising a bioabsorbable material with thromboresistant properties and a remodelable graft material. Preferably, the medical device is configured as an implantable stent graft with a bioabsorbable metallic frame attached to an extracellular matrix material. In particular, endovascularly-implantable stent grafts that are completely bioabsorbable within the body vessel after a desired period of time, are particularly desirable for treatment of conditions such as PVD or CLI.

SUMMARY

The invention relates to medical devices for implantation in a body vessel. Preferred embodiments of the invention relate to medical devices that include a frame comprising metallic bioabsorbable material. The frame can have any suitable configuration, and may include a plurality of interconnected struts and bends, or a woven tubular structure. Preferably, the frame has a substantially tubular structure defining a plurality of openings between struts arrayed along the surface of the frame. The medical devices are illustrated by discussion of medical devices comprising a bioabsorbable material comprising one or more metals, attached to a graft material. The graft material is preferably a remodelable material, such as an extracellular matrix material.

The metallic bioabsorbable material may provide several desirable properties to the medical device. First, support frame compositions comprising the metallic bioabsorbable materials are disclosed that provide a desirably low level of elastic recoil upon balloon expansion of the support frame within a body vessel, thereby mitigating possible trauma to the body vessel due to over-expansion of the support frame during deployment. Second, the metallic bioabsorbable support frames may provide a lower radial force to permit radial compression of the medical device in response to compression of the body vessel while maintaining vessel patency and preventing medical device migration within the body vessel. Medical device frames with lower radial force are particularly desirable for placement in the peripheral vascular system, where body vessels are prone to radial compression and torsion to a greater extent than in the coronary arterial system. Third, support frame compositions may be formulated to dissipate completely within the body vessel over a desired period of time, such as within about two, three, or four months. The rate of dissipation of the frame may be changed by altering the composition of the metallic bioabsorbable material. When the metallic bioabsorbable material is attached to a remodelable graft material, the medical device may provide for the autologous regrowth of a body vessel segment through the remodeling of the graft material. The support frame may provide support for the graft material during the remodeling process, maintaining the graft material in a configuration to permit remodeling and tissue growth in and through the graft material, and then dissipating within the body thereafter. For example, stent grafts comprising a metallic bioabsorbable support frame attached to a tubular extracellular matrix material may be implanted in a body vessel for a desired period of time to form a body vessel segment conforming to the shape of the graft material without any frame present after a period of time sufficient for dissipation of the metallic bioabsorbable material. Fourth, support frames compositions may include one or more metal components that function beneficially within the body upon release. For example, the presence of magnesium has been linked to a reduction in thrombus formation. Some metallic bioabsorbable compositions may release therapeutically beneficial amounts of magnesium during the dissipation of the support frame within the body vessel. Furthermore, the release of metal species from the metallic bioabsorbable materials may improve or promote remodeling processes in an attached graft material, such as an extracellular matrix material. Accordingly, the metallic bioabsorbable material may provide medical devices that provide any combination of one or more of the following advantages: providing a hypothrombogenic support frame, providing a desirably low level of elastic recoil upon implantation, providing a desirable amount of radial force to maintain vessel patency while prevent device migration but still permitting some desirable level of flexible compression of the body vessel to reduce inflammation or trauma, dissipating the support frame within the body vessel over a desired time period, and promoting desirable biological processes within the body vessel, such as the remodeling of an extracellular matrix graft material attached thereto or reducing inflammation of a body vessel in contact with the graft material or support frame.

The metallic bioabsorbable material can include various compositions disclosed herein. Preferably, the metallic bioabsorbable material includes one or more materials selected from a first group consisting of: magnesium, titanium, zirconium, niobium, tantalum, zinc and silicon. Also provided are mixtures and alloys of metallic bioabsorbable materials, including those selected from the first group.

The support frame preferably comprises a bioabsorbable metal containing magnesium. The bioabsorbable metal can also include magnesium, yttrium, rare earth metals, zirconium and/or lithium. Preferably, the rare earth metal is neodymium. One preferred bioabsorbable metal composition is an alloy formed from at least about 90% magnesium, about 3.5% to about 6.0% yttrium, and about 1.5% to about 5.0% rare earth metals and optionally comprises about 1% zirconium or lithium.

In a first embodiment, the medical devices for implantation in a body vessel comprising a metallic bioabsorbable material. Preferably, the support frame is attached to a graft material defining a tubular lumen, to form a stent graft. The metallic bioabsorbable material can be an alloy of two or more metals.

In one aspect of the first embodiment, the metallic bioabsorbable material can be an alloy of materials from a first group consisting of: magnesium, titanium, zirconium, niobium, tantalum, zinc and silicon, and a material selected from a second group consisting of: lithium, sodium, potassium, calcium, iron and manganese. The metallic bioabsorbable material from the first group may form a protective oxide coat upon exposure to blood or interstitial fluid. The material from the second group is preferably soluble in blood or interstitial fluid to promote the dissolution of an oxide coat. The bioabsorption rate, physical properties and surface structure of the metallic bioabsorbable material can be adjusted by altering the composition of the alloy. In addition, other metal or non-metal components, such as gold, may be added to alloys or mixtures of metallic bioabsorbable materials. Some preferred metallic bioabsorbable material alloy compositions include lithium-magnesium, sodium-magnesium, and zinc-titanium, which can optionally further comprise gold.

The frame itself, or any portion of the frame, can be made from one or more metallic bioabsorbable materials, and can further comprise one or more non-metallic bioabsorbable materials, as well as various non-bioabsorbable materials. The bioabsorbable material can be distributed throughout the entire frame, or any localized portion thereof, in various ways. In some embodiments, the frame can comprise a bioabsorbable material or a non-bioabsorbable material as a "core" material, which can be at least partially enclosed by other materials. The frame can also have multiple bioabsorbable materials stacked on all or part of the surface of a non-bioabsorbable core material. The frame can also comprise a surface area presenting both a bioabsorbable material and a non-bioabsorbable material.

The medical device can further include a graft material attached to a frame, for example to form a stent graft or a covered support frame. One or more graft materials can be attached to the frame to form a cylindrical outer and/or inner sleeve concentrically contacting a tubular frame. Preferably, the material attached to the frame comprises a remodelable material. Implanted remodelable material provides a matrix or support for the growth of new tissue thereon. Remodelable material may be absorbed into the body in which the device is implanted. Common events during the remodeling process include: widespread neovascularization, proliferation of granulation mesenchymal cells, and biodegradation/resorption of implanted remodelable material. Desirably, remodeling processes are substantially free of immune rejection. By this process, autologous cells from the body can replace the remodelable portions of the medical device. One particularly preferred graft material is an extracellular matrix material, such as the graft prosthesis materials disclosed in U.S. Pat. No. 6,206,931 to Cook et al.

Medical devices can be delivered intraluminally, for example using various types of delivery catheters, and expanded by conventional methods such as balloon expansion. The support frame is preferably moveable from a radially compressed configuration to a radially expanded configuration, and may have any suitable diameter. The medical devices are preferably configured to be balloon expanded within a body vessel from the compressed delivery configuration to the expanded deployment configuration. For example, a medical device can configured as a stent graft with a diameter in the radially expanded state of at least about 4 mm. Preferably, the support frame has an elastic recoil that minimizes undesirable trauma to a body vessel during implantation. Desirably, the elastic recoil of the support frame is less than 15%, preferably 10% or less and most preferably no more than about 4-8%.

Other embodiments provide methods of making medical devices described herein, such as methods of attaching the graft material to the frame. In a second embodiment, methods of manufacturing a medical device are provided. The medical device is preferably adapted for implantation in a body vessel. The manufacturing methods preferably comprise the steps of: providing a support frame comprising a metallic bioabsorbable material, the support frame defining a substantially tubular interior lumen, and attaching a graft material to the support frame, the graft material comprising an extracellular matrix material. In another aspect of the second embodiment, a method of manufacturing a medical device having a support frame is provided, the device being intended for use in the treatment of peripheral vascular disease through implantation in a body vessel, characterized in that the support frame is formed of a metallic bioabsorbable material. Preferably, the device consists of bioasorbable material, such as an extracellular matrix material. Other aspects relate to the use of a metallic bioabsorbable material for the manufacture of a medical device for use in the treatment of peripheral vascular disease through implantation in a body vessel. The use or method of manufacture may comprise the step of attaching to a support frame formed of a metallic bioabsorbable material to a graft material defining a tubular lumen. In another aspect, the medical device may consist of bioasorbable material or the medical device may consist of a metallic bioabsorbable material attached to an extracellular matrix material.

Still other embodiments provide methods of treating a subject, which can be animal or human, comprising the step of implanting one or more medical devices as described herein. In a third embodiment, methods of treatment are provided. Preferably, methods relating to the treatment of peripheral vascular disease are provided. The methods of treatment may comprise the step of intravascularly implanting a medical device in a body vessel, where the medical device comprises a support frame comprising a metallic bioabsorbable material and the medical device defines a substantially tubular interior lumen; and a tubular graft material attached to the support frame, the graft material comprising an extracellular matrix material.

Methods for delivering a medical device as described herein to any suitable body vessel are also provided, such as a vein, artery, biliary duct, ureteral vessel, body passage or portion of the alimentary canal. In some embodiments, medical devices having a frame with a compressed delivery configuration with a very low profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (e.g., renal, iliac, femoral, popliteal, subclavian, aorta, intracranial, etc.). Other nonvascular applications include gastrointestinal, duodenum, biliary ducts, esophagus, urethra, reproductive tracts, trachea, and respiratory (e.g., bronchial) ducts. These applications may optionally include a sheath covering the medical device.

The invention includes other embodiments within the scope of the claims, and variations of all embodiments, and is limited only by the claims made by the Applicants. Additional understanding of the invention can be obtained by referencing the detailed description of embodiments of the invention, below, and the appended drawings.

DETAILED DESCRIPTION

Figure 1A:
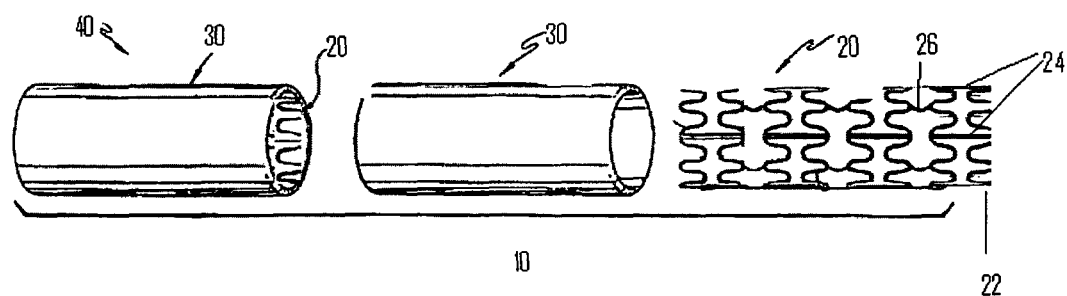
FIG. 1A is an exploded view of a first medical device embodiment comprising a tubular support frame and a graft prosthesis material attached to the interior of the support frame.

The following detailed description and appended drawings describe and illustrate various exemplary embodiments of the invention. The description and drawings serve to enable one skilled in the art to make and use the invention.

The invention provides medical devices for implantation in a body vessel which comprise a metallic bioabsorbable material, methods of making the medical devices, and methods of treatment that utilize the medical devices.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The invention relates to medical devices for implantation in a body vessel. More specifically, preferred embodiments of the invention relate to medical devices that include a frame comprising metallic bioabsorbable material.

A large number of different types of materials are known in the art which may be inserted within the body and later dissipate. The term "bioabsorbable" is used herein to refer to materials selected to dissipate upon implantation within a body, independent of which mechanisms by which dissipation can occur, such as dissolution, degradation, absorption and excretion. The terms "bioabsorbable," "bioabsorbable," "bioabsorbable," or "biodegradable" are used synonymously herein, unless otherwise specified, to refer to the ability of the material or its degradation products to be removed by biological events, such as by fluid transport away from the site of implantation or by cellular activity (e.g., phagocytosis). Only the term "bioabsorbable" will be used in the following description to encompass absorbable, absorbable, bioabsorbable, and biodegradable, without implying the exclusion of the other classes of materials.

"Non-bioabsorbable" material refers to a material, such as a polymer or copolymer, which remains in the body without substantial bioabsorption.

As used herein, the term "body vessel" means any body passage lumen that conducts fluid, including but not limited to blood vessels, esophageal, intestinal, billiary, urethral and ureteral passages.

The term "alloy" refers to a substance composed of two or more metals or of a metal and a nonmetal combined, for example by chemical or physical interaction, to form a material where the atoms of one or more of the combined materials may replace or occupy interstitial positions between the atoms of another material in the alloy. Alloys typically have physical and/or chemical properties that differ from the materials combined to form the alloy. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The terms "frame" and "support frame" are used interchangeably herein to refer to a structure that can be implanted, or adapted for implantation, within the lumen of a body vessel. Preferably, a frame functions as a stent. As used herein, a "stent" is any structure that is used to hold tissue in place within a body, including an interior portion of a blood vessel, lymph vessel, ureter, bile duct or portion of the alimentary canal. A "stent graft," as used herein, refers to a support frame attached to a graft material.

The term "graft material" as used herein refers to a flexible material that can be attached to a support frame, for example to form a stent graft. A graft material can have any suitable shape, but is preferably forms a tubular prosthetic vessel. A graft material can be formed from any suitable material, including the biologically derived or synthetic materials described herein.

Medical Device Configurations

The invention relates to medical devices that include an implantable frame including metallic bioabsorbable material. Preferred embodiments related to medical devices that include both an implantable metallic bioabsorbable support frame attached to a graft material. Most preferably, the graft material is a remodelable material.

Preferably, the medical device includes an intraluminally implantable frame defining a substantially cylindrical interior lumen. The frame can function as a support frame for an attached graft material. In one embodiment, the graft material is positioned on the exterior (abluminal) side of the medical device. FIG. 1A is an exploded view 10 of a first medical device 40 comprising a tubular support frame 20 and a graft material 30 attached to the exterior side of the support frame 20. The support frame 20 can be formed by a plurality of sinusoidal hoop members 22 longitudinally connected by a series of longitudinal connecting members including straight connecting members 24 and bent connecting members 26. The longitudinal connecting members 24, 26 can have any suitable configuration, including straight or arcuate members aligned substantially parallel to the longitudinal axis of the support frame 20. The support frame 20 can have any suitable dimension, but desirably may have a thickness of about 100-1,000 µm and preferably about 100-500 µm. The support frame 20 may be formed from an extruded bioabsorbable metallic material (such as a magnesium alloy), with a plurality of openings laser cut in the tube to form the plurality of sinusoidal hoop members 22 and longitudinal connecting members. The cross sectional area of the struts and bends is preferably substantially constant. Alternatively, portions of the struts or bends may have a greater cross sectional area than other support frame portions. Preferably, however, the largest cross sectional area of the support frame struts or bends is no more than about three times, and more preferably no more than about two times, the smallest cross sectional area.

Figure 1B:
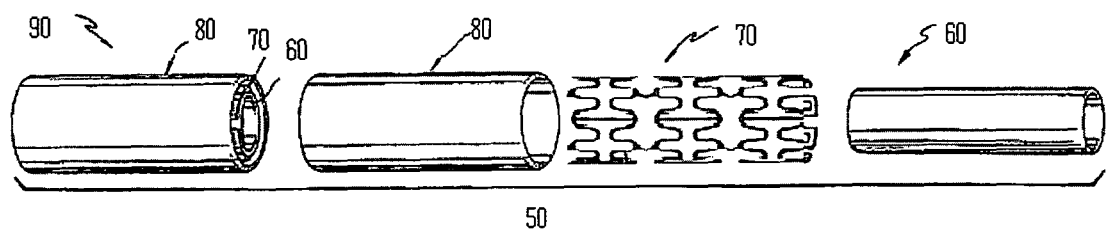
FIG. 1B is an exploded view of a second medical device embodiment comprising a tubular support frame positioned between an inner graft prosthesis material attached to the interior side of the support frame and an outer graft prosthesis material attached to the exterior side of the support frame.

The graft material 30 can be configured as a sleeve of remodelable material that is fitted around the exterior side of the support frame 20 to form the medical device 40 assembly. In another embodiment, the medical device includes a support frame and a graft materials attached to the interior (luminal) side of the support frame 20. The graft material is preferably configured as a sleeve or ring of material. Optionally, the medical device can include multiple graft materials attached to a support frame. FIG. 1B is an exploded view 50 of a second medical device 90 comprising a tubular support frame 70, a first graft material 60, and a second graft material 80 to form the medical device 90 assembly. The support frame 70 can be described with reference to the support frame 20 described in FIG. 1A. The second graft material 80 can be configured as a sleeve attached to the exterior (abluminal) side of the support frame 70. The second graft material 80 can be configured as an interior graft material attached to the interior of the support frame 70. The first graft material 60 can be configured for contact with fluid flow within a body vessel, while the second graft material 80 can be configured for contact with the wall of a body vessel. The first graft material 60 and the second graft material 80 can have any suitable thickness, but are preferably between about 5 and about 200 microns thick.

In one embodiment, the medical device is configured as a vascular stent for implantation within body vessel, such as an infrapopliteal artery. In another embodiment, the medical device is configured for implantation in a hemodialysis fistula.

Optionally, one or more bioactives can be included in a graft material or a support frame. Preferably, the graft material and the support frame include material that is remodelable and/or bioabsorbable within the body. Multiple illustrative examples of graft materials and support frames, as well as bioactives, are included below.

Metallic Bioabsorbable Materials

In a first embodiment, the implantable frame includes a metallic bioabsorbable material selected from a first group consisting of: magnesium, titanium, zirconium, niobium, tantalum, zinc and silicon. Also provided are mixtures and alloys of metallic bioabsorbable materials, including those selected from the first group. Various alloys of the materials in the first group can also be used as a metallic bioabsorbable material, such as a zinc-titanium alloy, for example, as discussed in U.S. Pat. No. 6,287,332 to Bolz et al.

The physical properties of the alloy can be controlled by selecting the metallic bioabsorbable material, or forming alloys of two or more metallic bioabsorbable materials. For example, the percentage by weight of titanium can be in the range of 0.1% to 1%, which can reduce the brittle quality of crystalline zinc. Without being bound to theory, it is believed that the addition of titanium leads to the formation of a $Zn_{15}Ti$ phase. In another embodiment, gold can be added to the zinc-titanium alloy at a percentage by weight of 0.1% to 2%, resulting in a further reduction of the grain size when the material cures and further improving the tensile strength of the material. These materials can be incorporated in the support frame of a medical device, including a medical device support frame.

In some embodiments, the metallic bioabsorbable material can be an alloy of materials from the first group and a material selected from a second group consisting of: lithium, sodium, potassium, calcium, iron and manganese. The metallic bioabsorbable material from the first group can form a protective oxide coating upon exposure to blood or interstitial fluid. The material from the second group is preferably soluble in blood or interstitial fluid to promote the dissolution of the oxide coating. Also provided are mixtures and alloys of metallic bioabsorbable materials, including those selected from the second group and combinations of materials from the first group and the second group. Further details relating to these metallic bioabsorbable materials are found in U.S. Pat. No. 6,287,332 to Bolz et al., which is incorporated herein by reference in its entirety.

In a second embodiment, the frame comprises a bioabsorbable metal composition containing magnesium. Preferred bioabsorbable metal compositions contain at least about 80% magnesium or more, including compositions with 85%, 86%, 87%, 88%, 89%, 90%, 91%, 92%, 93%, 94%, 95%, 96%, 97%, 98%, 99% or more magnesium, including increments of 0.1% magnesium content therebetween. Magnesium is believed to beneficially reduce incidence of inflammation or thrombus formation, and is believed to be beneficial in the remodeling process of extracellular matrix material within a body vessel. The magnesium-containing bioabsorbable metallic material can also include about 3.0%, 3.5%, 4.0%, 4.5%, 5.0%, 5.5% or 6.0% yttrium, or any interval of 0.1% between these compositions. The bioabsorbable metal can also include about 1.0%, 1.5%, 2.0%, 2.5%, 3.0%, 3.5%, 4.0%, 4.5%, 5.0% or about 5.0% rare earth metals. Rare earth metals include the lanthanide rare earth metals (lanthanum, cerium, praseodymium, neodymium, promethium, samarium, europium, gadolinium, terbium, dysprosium, holmium, erbium, thulium, ytterbium, lutetium) and the actinide rare earth metals (actinium, thorium, protactinium, uranium, neptunium, plutonium, americium, curium, berkelium, californium, einsteinium, fermium, mendelevium, nobelium and lawrencium). Preferably, the rare earth metal is a lanthanide rare earth metal. Most preferably, the rare earth metal is neodymium. The magnesium-containing bioabsorbable metallic material can also include about up to about 1% zirconium or lithium, including 0.1%, 0.2%, 0.3%, 0.4%, 0.5%, 0.6%, 0.7%, 0.8%, 0.9% and 1.0% zirconium.

The rate of dissolution of the metallic bioabsorbable material may vary depending on the composition of the alloy. The dissolution rate of the metallic bioabsorbable material within the body may be estimated by measuring its corrosion rate in various test solutions comprising suitable salt concentrations. For example, a corrosion rate of about 0.01-0.50, and preferably 0.1-0.2 $mg/cm^2/day$ in the ASTM B117 salt fog test, or about 0.1 $mg/cm^2/day$ in sea water immersion are suitable corrosion rates. Other embodiments provide stents having faster or slower corrosion rates and dissolution rates within the body. For example, a coronary stent formed from the bioabsorbable magnesium alloy AE21 was largely dissipated after 56 days post-implantation in porcine coronary arteries, according to Heublein et al., "Biocorrosion of magnesium alloys: a new principle of cardiovascular implant technology," *Heart*, 89:651-656 (2003). Magnesium alloys are believed to decompose according to the steady state reaction: $Mg+2H_2O=Mg(OH)_2+H_2$, thereby generating hydrogen.

A lower level of radial strength of biodegradable implants may improve the healing process. The support frame preferably has adequate radial strength to maintain patency of the tubular lumen defined by the graft material, with the least possible degree of recoil. The radial strength of the support frame is preferably low enough to prevent induction of an undesirable proliferation of smooth vessel muscle cells. Excessive mechanical stressing of vulnerable plaques within an artery may also induce formation a thrombus in the blood stream due to the issue of lipid particles, which may lead to acute infarct conditions.

One particularly preferred bioabsorbable metal is a magnesium alloy consisting essentially of: 3.7-4.3% yttrium, 2.4-

4.4% rare earth metals (including at least 2.0-2.5% neodymium, and preferably further comprising ytterbium, erbium, dysprosium and gadolinium), at least 0.4% zirconium and the balance magnesium. Other examples of magnesium-containing bioabsorbable metallic materials are described below, which comprise magnesium and the following materials:

1. 3-6% yttrium, 1-5% rare earth metal (e.g., lanthanum);
2. 3.7-4.3% yttrium, 2.4-4.4% rare earth metal (preferably lanthanum);
3. WE43 (3.7-4.3% yttrium, 2.4-4.4% neodymium, 0.4-1.% zirconium, 0-0.2% zinc, and remainder magnesium);
4. 3.7-5.5% yttrium, 1.5-4.4% rare earth metal (preferably lanthanum);
5. 4.0-5.0% yttrium, 1.5-4.0% rare earth metal (preferably lanthanum);
6. 4.75-5.50% yttrium, 1.5-4.0% rare earth metal (preferably lanthanum);
7. 3-6% yttrium, 1-5% rare earth metal (preferably lanthanum), 2-2.5% neodymium;
8. 3-6% yttrium, 1-5% rare earth metal (preferably lanthanum), 0.15-2.00% lithium, 0.4-1.0% zirconium, 0.004-0.200% zinc;
9. 4.1% yttrium, 3.1% lanthanum, 2.2% neodymium, 0.15% lithium, 0.55% zirconium, 0.10% zinc, 91.6% magnesium;
10. 5.1% yttrium, 2.8% lanthanum, 2.0% neodymium, 0.2% lithium, 0.7% zirconium, 0.2% zinc and 90.8% magnesium;
11. 0-5% neodymium, 0-40% lithium, 0-5% iron;
12. 2-5% aluminum, 1-4% rare earth metal (preferably neodymium), 0-12% lithium;
13. 2% aluminum, 1% rare earth metal (preferably neodymium), 6-12% lithium;
14. 2-4% aluminum, 1-2% rare earth metal (preferably neodymium), 0-8% lithium;
15. 8.5-9.5% aluminum, 0.45-0.90% zinc, and 0.15-0.40% manganese;
16. 4.5-5.3% aluminum, 0-5% rare earth metal (preferably neodymium), 30-40% lithium.

In the exemplary compositions enumerated above, any suitable amount of magnesium can be added to the composition unless the amount of magnesium is specifically indicated. All percentages are calculated by weight with respect to the total weight of the alloy composition. Where a preferred weight percentage for an alloy component includes a zero, the presence of the component in the alloy is optional (i.e., at "0%," the component is not present in the alloy). Preferably, the remainder of the composition by weight is magnesium, although trace amounts of other materials may also be added. Suitable commercially-available bioabsorbable magnesium metal alloys include WE43, AZ91D, AM50A, AE42 and AE21 (magnesium with 2% aluminum atoms and 1% rare earth elements Ce, Pr, Nd).

Other preferred bioabsorbable metal compositions are alloys formed from at least about 90% magnesium, about 3.7% to about 5.5% yttrium, and about 1.5% to about 4.4% rare earth metals and optionally comprising about 1% zirconium or lithium. Examples of suitable metallic bioabsorbable metals are disclosed in published U.S. Patent Application No. 2004/0098108 A1 to Harder et al., filed Nov. 11, 2003 and incorporated herein by reference in its entirety.

Other metallic bioabsorbable materials suitable for medical device support frames. For example, in one embodiment, the metallic bioabsorbable material comprises an alloy of lithium and magnesium with a magnesium-lithium ratio of about 60:40. The fatigue durability of the lithium:magnesium alloy can optionally be increased by the addition of further components such as zinc. In another embodiment, the medical device support frame comprises a sodium-magnesium alloy. U.S. Pat. No. 6,287,332 to Bolz et al., incorporated herein by reference in its entirety, provides additional examples of suitable bioabsorbable metal materials.

For instance, the metallic bioabsorbable material may be an alloy comprising zinc and calcium in a weight ratio of at least 21:1. Optionally, the alloy may further comprise up to about 3% of a nonmetal phosphorus. Another suitable bioabsorbable material is a ZnTi alloy with a Ti weight percentage of 0.1% to 1%. Optionally, gold can be added at a weight percentage of 0.1% to 2%, the Ti weight percentage remaining invariable, so that the stent consists of a ZnAuTi alloy. One preferred bioabsorbable metal support frame material is an alloy comprising a magnesium alloy with up to about 2% aluminum, such as about 0.1%-about 2% aluminum, and optionally further comprising up to about 1% of a rare earth metal (e.g., cerium, praseodymium, neodymium, promethium, and the like). Alternatively, the bioabsorbable material may be formed from a substantially pure zinc metal coating on a metal support frame, where the zinc coating is configured to dissolve without the formation of an oxide in the body. The zinc coating may be applied, for example, by electroplating zinc onto a stainless steel metal support frame. Desirably, the support frame may further comprise a gold coating on another portion of the stent, which may also be applied by electroplating or by laser welding. The presence of a gold coated frame portion may lead to active dissolution of the zinc portion of the frame upon implantation within a body vessel.

The frame itself, or any portion of the frame, can be made from one or more metallic bioabsorbable materials, and can further comprise one or more non-metallic bioabsorbable materials, as well as various non-bioabsorbable materials. The bioabsorbable material can be distributed throughout the entire frame, or any localized portion thereof, in various ways. In some embodiments, the frame can comprise a bioabsorbable material or a non-bioabsorbable material as a core material, which can be at least partially enclosed by other materials. The frame can also have multiple bioabsorbable materials positioned at least a portion of the surface of a non-bioabsorbable core material. The frame can also comprise a surface area presenting areas including a bioabsorbable material and other surfaces formed from a non-bioabsorbable material.

Preferably, the frame is an extruded or wrought magnesium alloy. Extruded magnesium alloys are believed to provide more desirable physiological effects than casting. For example, Harder et al. describe extruded magnesium alloys having desirable properties of promoting cultivation of cells on an extruded magnesium alloy in US 2004/0098108A1. Magnesium alloys can be produced by extrusion as magnesium sheet and plate, extruded profile or forged billet. The extruded magnesium alloy is preferably formed at a suitable temperature, extrusion ratio and extrusion speed, which can be optimized by one skilled in the art. Desirably, a billet material may be produced with a suitable level of grain refinement, preferably about 50-200 μm. Alternatively, the bioabsorbable metallic material may be formed by other methods, such as casting.

U.S. Pat. No. 4,116,731 to Tikhova et al., incorporated herein by reference with respect to the synthesis of magnesium alloys, describes one way to prepare magnesium alloys comprising yttrium, neodymium, zinc, zirconium and magnesium. For example, magnesium may be heated in a crucible with master alloys containing magnesium-zirconium, magnesium-neodymium, and magnesium-yttrium as follows. The master alloys may be prepared from yttrium and neodymium having a purity of 97% or greater. After melting the magnesium with any zinc at a suitable temperature (ca 760° C.), zinc and the magnesium-neodymium master alloy may be added and melted. The magnesium-zirconium master alloy can then be added portion-wise into the melt while stirring for 3-5 minutes. The magnesium-yttrium alloy can be added at a temperature of about 750-770° C., and the melt may be refined. The mixing preferably is done within about 10 minutes, and the melt may be poured into molds at about 730° C. to form the alloy. The alloy may be heat treated by hardening for dissolving excess phases in the solid solution at about 535° C. for 4-8 hours and cooling in a stream of air, followed by ageing at 200° C. for 12 hours. After such a treatment, no less than about 50% neodymium and yttrium typically enter the solid solution.

Metallic alloys with different melting points can also be made. For example, the extruded WE43 alloy has a melting point of about 560-640° C. and is preferably heat treated (T6) for 4-8 hours at 525° C., cooled in air (or hot water or polymer quench), aged for 16 hours at 250° C., air cooled.

Other Bioabsorbable Materials

In addition to a metallic bioabsorbable material, the frame can further comprise a bioabsorbable material, selected from any number of bioabsorbable homopolymers, copolymers, or blends of bioabsorbable polymers. In some embodiments, a medical device frame can comprise a biocompatible, bioabsorbable polymer or copolymer; a synthetic, biocompatible, non-bioabsorbable polymer or copolymer; or combinations thereof. In one embodiment, a medical device comprises a metallic bioabsorbable frame portion coated with a bioabsorbable polymer. The bioabsorbable polymer coating can dissolve within the body at a rate that is faster than the rate of dissolution of the metallic bioabsorbable material.

Several bioabsorbable, biocompatible polymers have been developed for use in medical devices, and have been approved for use by the U.S. Food and Drug Administration (FDA). In general, these materials biodegrade in vivo in a matter of months, although some more crystalline forms can biodegrade more slowly. These materials have been used in orthopedic applications, wound healing applications, and extensively in sutures after processing into fibers. More recently, some of these polymers also have been used in tissue engineering applications. A variety of bioabsorbable and biocompatible materials can be used to make medical device frames useful with particular embodiments disclosed herein, depending on the combination of properties desired. Properties such as flexibility, compliance, and rate of bioabsorption can be selected by choosing appropriate bioabsorbable materials. The properties of the bioabsorbable polymers may differ considerably depending on the nature and amounts of the comonomers, if any, employed and/or the polymerization procedures used in preparing the polymers.

Various polymers can be used incorporated into or coated on the support frame of a medical device. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; epoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS). Other examples of suitable bioabsorbable materials include: poly(glycolic acid), poly(lactic acid), poly(epsilon-caprolactone), poly(dimethyl glycolic acid), poly(hydroxy butyrate), polydioxanone, copolymers of polylactic acid and polyethyleneoxide, poly (lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polyhydroxyvalerate, poly(hydroxyalkanoates), poly(3-hydroxybutyrate), poly(4-hydroxybutyrate), poly(3-hydroxyvalerate), and poly(caprolactone), or poly(valerolactone), poly(1,3-dioxan-2-one), poly(6,6-dimethyl-1,4-dioxan-2-one), poly(1,4-dioxepan-2-one), and poly(1,5-dioxepan-2-one). Other examples of polymers that can be used in or on the frame include polyorthocarbonates, poly(amino acids) such as polylysine, and biodegradable polyphosphazenes such as poly(phenoxy-co-carboxylatophenoxy phosphazene).

Certain naturally occurring polymers can also be used in or on the frame, including: fibrin, fibrinogen, elastin, graft materials, chitosan, extracellular matrix (ECM), carrageenan, chondroitin, pectin, alginate, alginic acid, albumin, dextrin, dextrans, gelatins, mannitol, n-halamine, polysaccharides, poly-1,4-glucans, starch, hydroxyethyl starch (HES), dialdehyde starch, glycogen, amylase, hydroxyethyl amylase, cellulose, cellulose derivatives such as an alkyl cellulose (e.g., ethyl cellulose) and an alkoxycellulose (e.g., hydroxypropyl cellulose), amylopectin, glucoso-glycans, fatty acids (and esters thereof), hyaluronic acid, protamine, polyaspartic acid, polyglutamic acid, D-mannuronic acid, L-guluronic acid, zein and other prolamines, alginic acid, guar gum, and phosphorylcholine, as well as co-polymers and derivatives thereof.

Various cross linked polymer hydrogels can also be used to form or coat the frame. A hydrogel can be formed, for example, using a base polymer selected from any suitable polymer, preferably poly(hydroxyalkyl (meth)acrylates), polyesters, poly(meth)acrylamides, poly(vinyl pyrollidone) and poly(vinyl alcohol). A cross-linking agent can be one or more of peroxides, sulfur, sulfur dichloride, metal oxides, selenium, tellurium, diamines, diisocyanates, alkyl phenyl disulfides, tetraalkyl thiuram disulfides, 4,4'-dithiomorpholine, p-quinine dioxime and tetrachloro-p-benzoquinone. Also, boronic acid-containing polymer can be incorporated in hydrogels, with optional photopolymerizable group, into degradable polymer, such as those listed above.

Incorporation of Bioactive Materials

Optionally, the support frame or graft material can include one or more bioactive materials. The bioactive material can be selected to treat indications such as coronary artery angioplasty, renal artery angioplasty, carotid artery surgery, renal dialysis fistulae stenosis, or vascular graft stenosis. The maximal dosage of the therapeutic to be administered is the highest dosage that effectively inhibits inflammatory or promotes healing activity, but does not cause undesirable or intolerable side effects. Undesirably side effects include clinically significant antimicrobial or antibacterial activity, as well as toxic effects. For example, a dose in excess of about 50 mg/kg/day would likely produce side effects in most mammals, including humans. The dosage of the bioactive agent or agents used will vary depending on properties of the coating, including its time-release properties, whether the coating is itself biodegradable, and other properties. Also, the dosage of the bioactive agent or agents used will vary depending on the potency, pathways of metabolism, extent of absorption, half-life, and mechanisms of elimination of the bioactive agent itself. In any event, the practitioner is guided by skill and knowledge in the field, and embodiments according to the present invention include without limitation dosages that are effective to achieve the described phenomena. The bioactive agent or agents may be linked by occlusion in the matrices of the graft material or a coating applied to the graft material and/or frame, bound by covalent linkages, or encapsulated in microcapsules. Within certain embodiments, the bioactive agent or agents are provided in non-capsular formulations such as microspheres (ranging from nanometers to micrometers in size), pastes, threads of various size, films and sprays. Within certain aspects, a coating may be formulated to deliver the bioactive agent or agents over a period of several hours, days, or, months. For example, "quick release" or "burst" coatings are provided that release greater than 10%; 20%, or 25% (w/v) of the bioactive agent or agents over a period of 7 to 10 days. Within other embodiments, "slow release" bioactive agent or agents are provided that release less than 1% (w/v) of a bioactive agent over a period of 7 to 10 days. Further, the bioactive agent or agents of the present invention should preferably be stable for several months and capable of being produced and maintained under sterile conditions.

Bioactive agents may be fashioned in any size ranging from 50 nm to 500 µm, depending upon the particular use. Alternatively, such compositions may also be readily applied as a "spray", which solidifies into a film or coating. Such sprays may be prepared from microspheres of a wide array of sizes, including for example, from 0.1 µm to 3 µm, from 10 µm to 30 µm, and from 30 µm to 100 µm. Within yet other aspects, the bioactive agent compositions may be formed as a film applied to the graft material or frame. Preferably, such films are generally less than 5, 4, 3, 2, or 1 mm thick, more preferably less than 0.75 mm, 0.5 mm, 0.25 mm, or, 0.10 mm thick. Films can also be generated of thicknesses less than 50 µm, 25 µm or 10 µm. Such films are preferably flexible with a good tensile strength (e.g., greater than 50, preferably greater than 100, and more preferably greater than 150 or 200 N/cm2), have good adhesive properties (i.e., adhere to moist or wet surfaces), and have controlled permeability. Optionally, the coating may be mixed with or coated with a physical barrier. Such barriers can include inert biodegradable materials such as gelatin, PLGA/MePEG film, PLA, or polyethylene glycol among others. In the case of PLGA/MePEG, once the PLGA/MePEG becomes exposed to blood, the MePEG will dissolve out of the PLGA, leaving channels through the PLGA to underlying layer of biologically active substance (e.g., poly-1-lysine, fibronectin, or chitosan), which then can initiate its biological activity.

The bioactive materials can be attached to the medical device in any suitable manner. For example, a bioactive can be attached to the surface of the medical device, or be positioned within the support frame or graft material in pores. Referring again to FIG. 1B, one or more bioactive agents can be coated on or impregnated in the support frame 70, the first graft material 60 or the second graft material 80. The bioactive agent can be selected to perform one or more desired biological functions. For example, the second graft material 80 can comprise a bioactive selected to promote the ingrowth of tissue from the interior wall of a body vessel, such as a growth factor. An anti-angiogenic or antineoplastic bioactive such as paclitaxel, sirolimus or a rapamycin analog, or a metalloproteinase inhibitor such as batimastat can be incorporated in or coated on the support frame 70 or second graft material 80 to mitigate or prevent undesired conditions in the vessel wall, such as restenosis. Many other types of bioactive agents can be incorporated in a graft material or a support frame.

Bioactive materials for use in bio-compatible coatings include those suitable for coating on an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

A bioactive material can be one or more pro-healing therapeutic agents, which include materials that provide or promote endothelial cell seeding. For instance, coatings comprise antibodies to CD34 receptors on progenitor circulating endothelial cells. Nitric oxide, vascular endothelial growth factor, and 17-β-estradiol are other examples of prohealing therapeutic agents. Another prohealing bioactive agent is vascular endothelial growth factor (VEGF). VEGF is an endothelial cell-specific mitogen, and a cytokine involved in processes essential to the growth, maintenance and repair of vascular structures. VEGF can be coated on an implantable frame, an attached graft material or both. Local drug delivery of VEGF from a medical device, such as a stent frame, can reduce in-stent restenosis. Other examples of pro-healing therapeutic agents, along with methods for coating the same on implantable medical devices, are provided in published U.S. Patent Application Nos. 2004/0092440 (filed Nov. 8, 2002, by Weinstein) (described below); 2005/0191333 (filed Apr. 28, 2005 by Hsu) (such as stearylkonium heparin, benzalkonium heparin, or tridodecylmethyl ammonium heparin); and 2005/0148585 (filed Aug. 26, 2004 by Davies et al.), which are incorporated herein by reference.

In another aspect, the bioactive material comprises a cGMP PDE5 inhibitor, including those described in 2005/0148585 (filed Aug. 26, 2004 by Davies et al.). Elevated levels of the enzyme cGMP PDE5 may be found in wounded tissue, particularly where the tissue is inflamed or scarred. Other suitable cGMP PDE5 inhibitors include: the pyrazolo[4,3-d]pyrimidin-7-compounds disclosed in EP-A-0463756; the pyrazolo[4,3-d]pyrimidin-7-one compounds disclosed in EP-A-0526004; the pyrazolo[4,3-d]pyrimidin-7-one compounds disclosed in published international patent application WO 93/06104; the isomeric pyrazolo[3,4-d]pyrimidin-4-o-nes disclosed in published international patent application WO 93/07149; the quinazolin-4-one compounds disclosed in published international patent application WO 93/12095; the pyrido[3,2-d]pyrimidin-4-one compounds disclosed in published international patent application WO 94/05661; the purin-6-one compounds disclosed in published international patent application WO 94/00453; the pyrazolo[4,3-d]pyrimidin-7-one compounds disclosed in published international patent application WO 98/49166; the pyrazolo[4,3-d]pyrimidin-7-one compounds disclosed in published international patent application WO 99/54333; the pyrazolo

[4,3-d]pyrimidin-4-one compounds disclosed in EP-A-0995751; the pyrazolo[4,3-d]pyrimidin-7-one compounds disclosed in published international patent application WO 00/24745; the pyrazolo[4,3-d]pyrimidin-4-one compounds disclosed in EP-A-0995750; the compounds disclosed in published international application WO95/19978; the compounds disclosed in published international application WO 99/24433 and the compounds disclosed in published international application WO 93/07124, the portions of which pertaining to the preparation of these compounds are incorporated herein by reference.

In one preferred embodiment, the bioactive material is an immunophilin ligand effective to promote healing of the wound in the subject, such as one or more compounds selected from the group consisting of: a member of the FK506-binding protein (FKBP) family of peptidylprolyl cis-trans isomerases (including FK506, or "tacrolimus"), and a nonimmunosuppressive immunophilin ligand (including GPI-1046 and V10,367). As endogenous intracellular receptors, immunophilins include FK506-binding proteins (FKBPs) and cyclophilins. FK506 (tacrolimus) (Fujisawa Pharmaceutical Co., Ltd, Osaka, Japan) is an immunosuppressive drug that promotes nerve regeneration, and binds with high affinity to immunophilins (See Kay, J. E., "Structure-function relationships in the FK506-binding protein (FKBP) family of peptidylprolyl cis-trans isomerases," Biochem. J., 314:361-85 (1996) and Gold, B. G., "FK506 and the role of immunophilins in nerve regeneration," Mol. Neurobiol., 15:285-306 (1997); and Jost et al., "Acceleration of peripheral nerve regeneration following FK506 administration," Restor. Neurol. Neurosci., 17:39-44 (2000)). Immunophilins are proteins with peptidyl-proline cis/trans isomerase activity (Galat and Metcalfe, Peptidylproline cis/trans isomerases. Prog. Biophys. Mol. Biol., 63:67-118, 1995; Marks, A. R., Cellular functions of immunophilins. Physiol. Rev., 76:631-49, 1996). Among these compounds are the Vertex drug, V10,367 (Vertex Pharmaceuticals, Cambridge Mass.), the Guilford compound, GPI-1046 (Guilford Pharmaceuticals, Baltimore, Md.), and GM-284, described in published U.S. Patent Application Nos. 2004/0092440 (filed Nov. 8, 2002, by Weinstein). GM-284 has the following chemical structure:

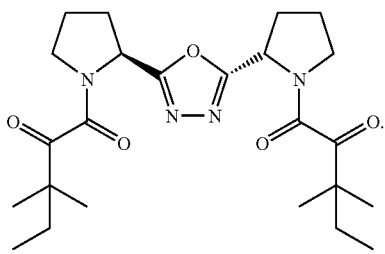

Medical devices comprising an antithrombogenic bioactive material are particularly preferred for implantation in areas of the body that contact blood. An antithrombogenic bioactive material is any bioactive material that inhibits or prevents thrombus formation within a body vessel. The medical device can comprise any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

One or more bioactives can be coated on or incorporated within a support frame or graft material by any suitable technique. In one embodiment, a graft material or support frame can be configured to absorb a solution of a bioactive material. For instance, a graft material with absorbent properties can be selected, or a portion of a medical device can be coated with a cross-linked polymer hydrogel material to retain a bioactive material for elution within a body vessel. A bioactive can be incorporated by soaking the absorbent portion of the medical device in a solution of the bioactive material and allowing the absorption of the bioactive solution. Subsequently, the solvent can be evaporated to leave the bioactive within the medical device.

In another embodiment, a graft material or support frame can also be coated with or formed from a biodegradable polymers, as well as copolymers of degradable polymers. A bioactive material can be mixed with or copolymerized with the bioabsorbable polymer. Alternatively, the bioactive material or a mixture of bioactive material and biostable or bioabsorbable polymer can be coated with a second layer comprising a bioabsorbable polymer. Upon implantation, absorption of the bioabsorbable polymer releases the bioactive. Bioabsorbable polymers can be formed by copolymerization of compatible monomers or by linking or copolymerization of functionalized chains with other functionalized chains or with monomers. Examples include crosslinked phosphorylcholine-vinylalkylether copolymer and PC-Batimastat copolymers.

In one embodiment, the frame is coated with a coating of between about 1 µm and 50 µm, or preferably between 3 µm and 30 µm, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier is a bioabsorbable material, and one preferred carrier is poly-L-lactic acid. U.S. patent application Ser. No. 10/639,225, filed Aug. 11, 2003 and published as US2004/0034409A1 on Feb. 19, 2004, describes methods of coating a bioabsorbable metal support frame with bioabsorbable materials such as poly-L-lactic acid that are incorporated herein by reference.

Additional Frame Materials

In addition to a metallic bioabsorbable metal, the support frame can be formed from or coated with other metal or non-metal materials. In some embodiments, a support frame can be formed from a biostable biocompatible metal such as nitinol, cobalt-chromium or stainless steel, coated with a metallic bioabsorbable material. Alternatively, portions of a support frame can comprise a core layer of a metallic bioabsorbable metal material surrounded or partially covered by a bioabsorbable metallic material. The support frame can also be formed from mixtures of metallic bioabsorbable materials and one or more other biocompatible materials.

Examples of materials that can be used to form a frame, or can be coated on a frame, include biocompatible metals or other metallic materials, stainless steels (e.g., 316, 316L or 304), nickel-titanium alloys including shape memory or superelastic types (e.g., nitinol or elastinite), noble metals including platinum, gold or palladium, refractory metals including tantalum, tungsten, molybdenum or rhenium, stainless steels alloyed with noble and/or refractory metals, silver, rhodium, inconel, iridium, niobium, titanium, magnesium, amorphous metals, plastically deformable metals (e.g., tantalum), nickel-based alloys (e.g., including platinum, gold and/or tantalum alloys), iron-based alloys (e.g., including platinum, gold and/or tantalum alloys), cobalt-based alloys (e.g., including platinum, gold and/or tantalum alloys), cobalt-chromium alloys (e.g., elgiloy), cobalt-chromium-nickel alloys (e.g., phynox), alloys of cobalt, nickel, chromium and molybdenum (e.g., MP35N or MP20N), cobalt-chromium-vanadium alloys, cobalt-chromium-tungsten alloys, platinum-iridium alloys, platinum-tungsten alloys, magnesium alloys, titanium alloys (e.g., TiC, TiN), tantalum alloys (e.g., TaC, TaN), L605, and magnetic ferrite.

The support frame or graft material can be coated with various biocompatible materials, including bioabsorbable or biostable polymers described above as bioabsorbable coating materials. Examples of nonmetallic biocompatible coating materials that may be coated on or incorporated into a support frame include: polyamides, polyolefins (e.g., polypropylene or polyethylene), parylene, silane, polyurethane, polyorthoester, polyether sulfone, polycarbonate, polytetrafluoroethylene, polyethylene terephthalate (e.g., dacron or mylar); expanded fluoropolymers (e.g., polytetrafluoroethylene (PTFE)); fluorinated ethylene propylene (FEP); polyphosphazene. One preferred example of a polymeric coating comprises a poly(styrene-b-isobutylene-b-styrene) block copolymer deposited on a 1,3-di(2-methoxy-2-propyl)-5-tert-butylbenzene. Other suitable coatings are N-(3,4-dimethoxycinnamoyl)anthranilic acid, and phosphorylcholine. In one embodiment, the frame can comprise silicon-carbide (SiC). For example, published U.S. Patent Application No. US2004/034409 to Hueblein et al., published on Feb. 14, 2004 and incorporated in its entirety herein by reference, discloses various suitable frame materials and configurations.

Any of the coatings described herein can optionally be mixed with one or more bioactive materials and coated on a support frame or graft material. In some embodiments, a frame comprises a core or "base" material surrounded by, or combined, layered, or alloyed with a metallic bioabsorbable material.

Support Frame Structures

Figure 2A:
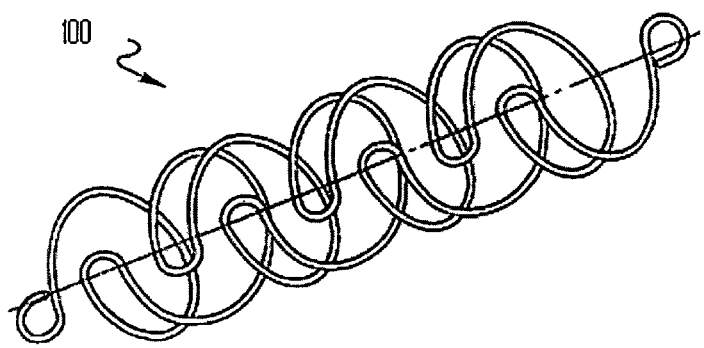
FIG. 2A is a diagram of a first medical device frame formed from a wire frame bent in a serpentine geometry.
Figure 2B:
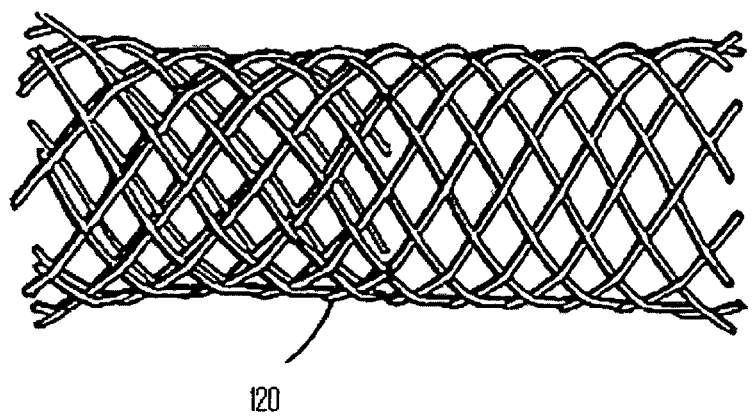
FIG. 2B shows a second medical device frame having a braided configuration.
Figure 2C:
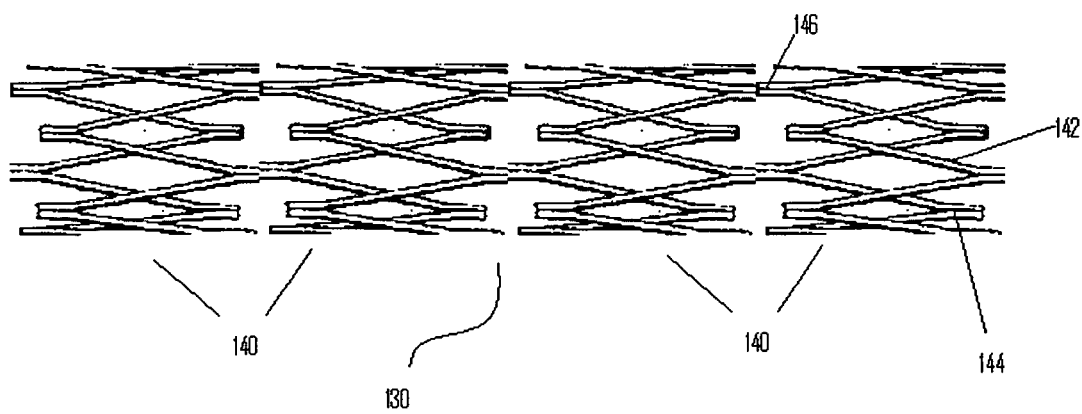
FIG. 2C shows a fourth medical device frame formed by joining a series of hoops formed from a plurality of interconnecting struts.

The frame can have any suitable configuration, but is preferably shaped and configured to maintain a graft material in a desired configuration or orientation within the body vessel. In some embodiments, the frame comprises a plurality of interconnected struts and bends, which can be of any suitable structure or orientation. In one embodiment, the frame comprises a plurality of struts connected by alternating bends. For example, the frame can be a sinusoidal ring member comprising a series of struts in a "zig-zag" or sinusoidal pattern. The frame can also comprise multiple ring members with struts in a "zig-zag" or sinusoidal pattern, for example by connecting the ring members end to end, or in an overlapping fashion. In some embodiments, the struts are substantially aligned along the surface of a tubular plane, substantially parallel to the longitudinal axis of the support frame. FIG. 2A is a diagram of a medical device frame 100 formed from a wire frame bent in a serpentine geometry. FIG. 2B shows a second medical device frame 120 having a braided configuration. FIG. 2C shows a fourth medical device frame 130 formed by joining a series of hoops 140 formed from a plurality of interconnecting struts 142 connected by bends or joined portions 144. The medical device frame 130 includes a plurality of hoops 140 are joined by longitudinal connecting members 146. Certain non-limiting examples of frame embodiments are provided herein to illustrate selected features of the medical devices relating to component frames. Medical devices can comprise the frame embodiments discussed below, and combinations, variations or portions thereof, as well as other frame configurations. Medical devices comprising various frames in combination with material suitable to form a leaflet attached thereto are also within the scope of some embodiments of the invention. Other examples of suitable frame shapes are provided in U.S. Pat. Nos. 6,508,833 and 6,200,336 to Pavcnik, and U.S. patent application Ser. Nos. 10/721,582, filed Nov. 25, 2003; 10/642,372, filed Aug. 15, 2003; and 10/294,987, filed Nov. 14, 2002, all of which are incorporated herein by reference in their entirety. Other suitable frame structures can be selected from implantable frame structures disclosed in U.S. Pat. Nos. 6,730,064; 6,638,300; 6,599,275; 6,565,597; 6,530,951; 6,524,336; 6,508,833; 6,464,720; 6,447,540; 6,409,752; 6,383,216; 6,358,228; 6,336,938; 6,325,819; 6,299,604; 6,293,966; 6,200,336; 6,096,070; 6,042,606; 5,800,456; 5,755,777; 5,632,771; 5,527,354; 5,507,771; 5,507,767; 5,456,713; 5,443,498; 5,397,331; 5,387,235; 5,530,683; 5,334,210; 5,314,472; 5,314,444; 5,282,824; 5,041,126; and 5,035,706; all assigned to Cook Inc. and incorporated in their entirety herein by reference. These frame shapes can be formed from the metallic bioabsorbable materials disclosed herein, and can be attached to a graft material. An example of a suitable metallic bioabsorbable metal support structure is provided by U.S. patent application Ser. No. 10/706,717, filed Nov. 11, 2003 by Harder et al., and published as US2004/0098108A1 on May 20, 2004.

The dimensions of the implantable support frame will depend on its intended use. Typically, the implantable frame will have a length in the range from 4 mm to 140 mm for vascular applications. The small (radially collapsed) diameter of a cylindrical frame will usually be in the range from about 1 mm to 10 mm, more usually being in the range from 1.5 mm to 6 mm for vascular applications. The expanded diameter will usually be in the range from about 2 mm to 30 mm, preferably being in the range from about 2.5 mm to 15 mm for vascular applications. For example, a stent graft for implantation in a peripheral artery may have expanded diameters of about 7-8 mm (carotid), 4-6 mm (femoral), 2-3 mm (popliteal) or 8-9 mm (illiac), depending on the site of implantation. The dimensions of the individual struts of the support frame are preferably about 100 µm-1,000 µm, more preferably about 200-500 µm.

The medical devices of some embodiments can be expandable from a compressed delivery configuration to an expanded deployment configuration. Preferably, the support frame can be radially compressed prior to implantation in a human or animal vessel. The support frame is preferably configured to be radially compressed with a force that is typical of compression encountered within a body vessel at a treatment site. After implantation, upon release of a radial compression force, the support frame structure elastically recoils toward its original configuration, until it meets the wall of the body vessel. The structure provides flexibility which allows the support frame to follow the curvature of the vessel which receives it. The metallic bioabsorbable material desirably has a radial elastic recoil that is suitably low to minimize undesirable irritation to the wall of a body vessel, while maintaining adequate patency of the body vessel for an intended medical purpose. The term "radial strength" is used to denote an internal resistance on the part of the support frame in a radially expanded condition in response to radially acting forces directed to cause radial compression of the implant. Radial strength can be quantitatively expressed by specifying a collapse pressure. In that respect the implants of the state of the art exhibit a collapse behavior in which compression takes place abruptly, that is to say when the collapse pressure is reached the implant collapses very quickly.

Medical devices can be delivered intraluminally, for example using various types of delivery catheters, and be expanded by conventional methods such as balloon expansion or self-expansion. The medical devices are typically radially expandable by inflating a catheter balloon within the lumen of the graft material. In order to avoid unnecessary vessel damage it is also desirable that, after expansion and after removal of the balloon, the degree to which the support frame elastically springs back (elastic recoil) is desirably minimized in order to minimize the amount of radial stent expansion beyond the final resting expanded diameter of the implanted medical device. As used with reference to a medical device (or portion thereof) herein, the term "elastic recoil" refers to the tendency of the medical device to return to a radially expanded state after release of a radially compressive force. For example, fully radially expanded support frames may have a radial elastic recoil 10% or less, preferably about 9, 8, 7, 6, 5, 4% radial elastic recoil, or less for many peripheral vascular implantation sites. For example, an elastic recoil of about 5% and a collapse pressure of 0.8 atm. may be obtained from a 3 mm (diameter)×15 mm tubular support frame formed from an extruded wrought WE43 magnesium alloy having a plurality struts with thicknesses of about 150-200 mm formed by laser cutting. In contrast, bioabsorbable polymeric support frame materials such as a poly(lactic acid)-poly(caprolactone) (PLA/PCL) typically have an elastic recoil of greater than 15% or more. The metallic bioabsorbable material desirably has a collapse pressure comparable to metal stents. For example, bioabsorbable metal support frames may have a crush pressure of about 300-1,000 mmHg, preferably about 300-500 mmHg, prior to implantation.

Figure 3A:
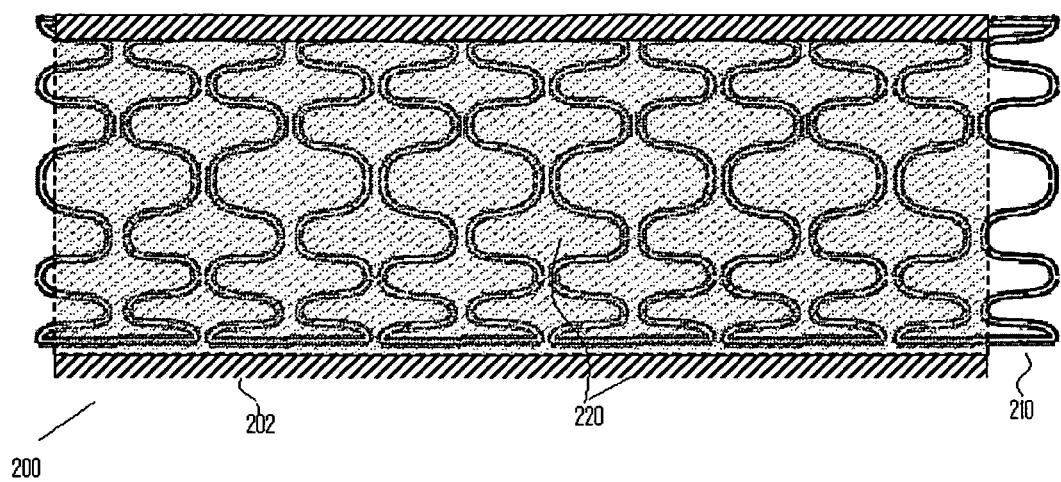
FIG. 3A shows a side view of a medical device comprising a frame and an outer graft material in an expanded state.

Examples of balloon expandable frame materials include the bioabsorbable metals described herein. The metallic bioabsorbable materials can be coated on a balloon expandable metal structures such as those formed from stainless steel or cobalt-chromium. Alternatively, the metallic bioabsorbable material can be coated on a self-expanding material such as the nickel-titanium alloy Nitinol. FIG. 3A shows a side view of a medical device 202 comprising a support frame 210 and a graft material 220 in an expanded state 200. The support frame 210 comprises a plurality of sinusoidal hoop members connected longitudinally to define a cylindrical interior lumen. The graft material 220 is configured as a tubular sleeve attached to the exterior surface of the support frame 210.

Figure 3B:
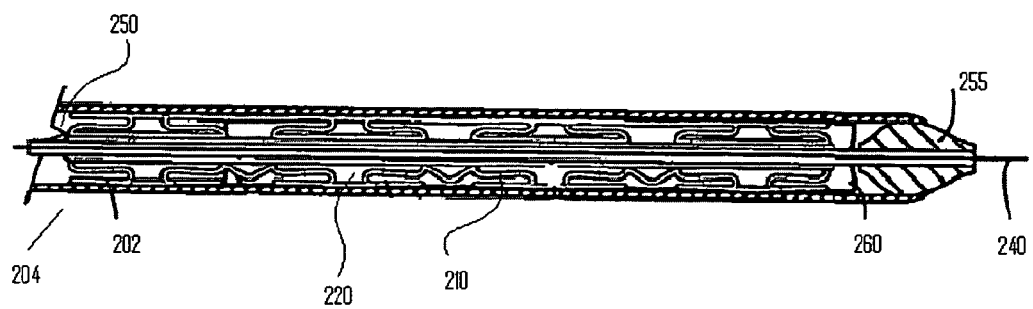
FIG. 3B shows the medical device of FIG. 3A in a compressed or delivery configuration within the distal end of a delivery catheter.
Figure 4:
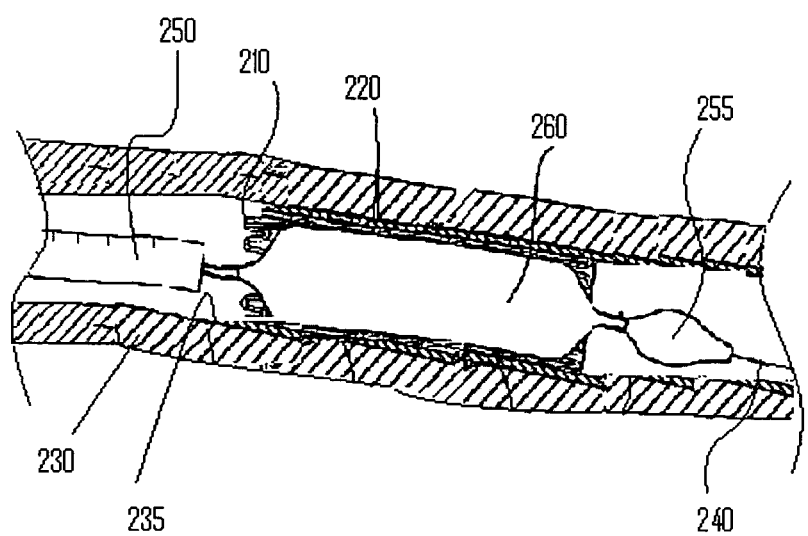
FIG. 4 shows the deployment of the medical device shown in FIG. 3B by balloon expansion within a body vessel.

FIG. 3B shows the medical device 202 of FIG. 3A in a radially compressed configuration 204 within the distal end of a delivery catheter 250. The delivery catheter 250 includes a balloon 260 annularly enclosed by the medical device 202 and radially inflatable. The delivery catheter 250 is fitted over a guidewire 240 for delivery to a blood vessel such as an artery or vein by conventional percutaneous transluminal methods. The distal portion of the delivery catheter 250 can be placed within a body vessel at a desired point of treatment, and the balloon 260 can be inflated. FIG. 4 shows the deployment 300 of the medical device 202 shown in FIG. 3B by expansion of the balloon 260 within a body vessel 230. The catheter 250 is positioned at a point of treatment 300 within a body vessel 230. The balloon 260 is then inflated to expand the medical device 202 to the expanded configuration shown in FIG. 3A. Upon inflation of the balloon, the graft material 220 contacts the interior surface 235 of the body vessel 230. Subsequently, the balloon 260 can be deflated and the delivery catheter 250 removed from the body vessel 230 along the guidewire 240.

Alternatively, the support frame 210 can comprise a self-expanding material such as nitinol, coated with a metallic bioabsorbable material. A medical device 202 comprising a self-expanding support frame 210 can be deployed from a catheter that includes a moveable sheath containing the support frame instead of a balloon. The sheath can be longitudinally translated with respect to the medical device, away from the distal end of the delivery catheter. When the sheath no longer covers the medical device, the self-expanding support frame can radially expand to contact the inner wall of the body vessel, where the medical device can be maintained by the outward force exerted by the frame or by barbs or perforations in the exterior surface of the medical device.

The frame can also comprise a means for orienting the frame within a body lumen, such as a radiopaque region. For example, the frame can comprise a marker, or a delivery device comprising the frame can provide indicia relating to the orientation of the frame within the body vessel. The marker can be a radiopaque portion of the frame detectable by imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Radiopaque, physiologically compatible materials include metals and alloys selected from the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible. Highly preferred is a platinum/tungsten alloy, e.g., 8% tungsten and the remainder platinum. The particular form and choice of material used for the implantable frame will depend on the desired application.

The medical devices of the embodiments described herein may be oriented in any suitable absolute orientation with respect to a body vessel. The recitation of a "first" direction is provided as an example. Any suitable orientation or direction may correspond to a "first" direction. The medical devices of the embodiments described herein may be oriented in any suitable absolute orientation with respect to a body vessel. For example, the first direction can be a radial direction in some embodiments.

Graft Materials

Preferably, a medical device can comprise a frame and a material attached to the frame. The material can form one or more tubular grafts contacting the outside (abluminal) and/or the interior (luminal) surface of the frame.

The graft material preferably comprises a remodelable material. A variety of remodelable materials are available for use in implantable medical devices. Extracellular matrix material (ECM) is one category of remodelable material. Naturally derived or synthetic graft materialous materials can be used to provide remodelable surfaces on implantable medical devices. Naturally derived or synthetic graft materialous material, such as extracellular matrix material, are another category of remodelable materials that include, for instance, submucosa, renal capsule membrane, dura mater, pericardium, serosa, and peritoneum or basement membrane materials. One specific example of an extracellular matrix material is small intestine submucosa (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts.

The compositions provided herein comprise an extracellular matrix (ECM) material can be derived from a variety of suitable sources. Preferably, the ECM material is a remodelable material. The terms "remodelable" or "bioremodelable" refer to the ability of a material to allow or induce host tissue growth, proliferation or regeneration following implantation of the tissue in vivo. Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization are typically observed over a period of about 5 days to about 6 months or longer, as the remodelable material acts as a matrix for the ingrowth of adjacent tissue with site-specific structural and functional properties. The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately.

One preferred category of ECM material is submucosal tissue. Submucosal ECM material can be obtained from any suitable source, including without limitation, intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine. More preferably, the ECM material is Tela submucosa, which is a layer of graft material-containing connective tissue occurring under the mucosa in most parts of the alimentary, respiratory, urinary and genital tracts of animals. Examples of suitable ECM materials include renal capsule matrix (RCM), urinary bladder matrix (UBM) and most preferably small intestine submucosa (SIS). Most preferably, the ECM material is obtained from processed intestinal graft material layer derived from the tunic submucosa of porcine small intestine.

As used herein, "tela submucosa" refers to a layer of graft material-containing connective tissue occurring under the mucosa in most parts of the alimentary, respiratory, urinary, integumentary, and genital tracts of animals. Tela submucosa, as with many animal tissues, is generally aseptic in its natural state, provided the human or animal does not have an infection or disease. This is particularly the case since the tela submucosa is an internal layer within the alimentary, respiratory, urinary and genital tracts of animals. Accordingly, it is generally not exposed to bacteria and other cellular debris such as the epithelium of the intestinal tract. Preferably, the tela submucosa tissue ECM materials, which are graft material-based and thus predominantly graft material, are derived from the alimentary tract of mammals and most preferably from the intestinal tract of pigs. A most preferred source of whole small intestine is harvested from mature adult pigs weighing greater than about 450 pounds. Intestines harvested from healthy, nondiseased animals will contain blood vessels and blood supply within the intestinal tract, as well as various microbes such as *E. coli* contained within the lumen of the intestines. Therefore, disinfecting the whole intestine prior to delamination of the tela submucosa substantially removes these contaminants and provides a preferred implantable tela submucosa tissue which is substantially free of blood and blood components prior to incorporation into a stent graft structure, as well as any other microbial organisms, pyrogens or other pathogens that may be present. In effect, this procedure is believed to substantially preserve the inherent aseptic state of the tela submucosa, although it should be understood that it is not intended that the present invention be limited by any theory.

Additional information as to submucosa materials useful as ECM materials herein can be found in U.S. Pat. Nos. 4,902,508; 5,554,389; 5,993,844; 6,206,931; 6,099,567; and 6,375,989, as well as published U.S. Patent Applications US2004/0180042A1 and US2004/0137042A1, which are all incorporated herein by reference. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

The ECM material can be isolated from biological tissue by a variety of methods. In general, an ECM material can be obtained from a segment of intestine that is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use as described below. The resulting submucosa tissue typically has a thickness of about 100-200 micrometers, and may consist primarily (greater than 98%) of acellular, eosinophilic staining (H&E stain) ECM material.

Preferably, the source tissue for the remodelable material is disinfected prior to delamination by using the preparation disclosed in U.S. Pat. No. 6,206,931, filed Aug. 22, 1997 and issued Mar. 27, 2001 to Cook et al., and US Patent Application US2004/0180042A1 by Cook et al., filed Mar. 26, 2004, published Sep. 16, 2004 and incorporated herein by reference in its entirety. Most preferably, the tunica submucosa of porcine small intestine is processed in this manner to obtain the ECM material. This method is believed to substantially preserve the aseptic state of the tela submucosa layer, particularly if the delamination process occurs under sterile conditions. Specifically, disinfecting the tela submucosa source, followed by removal of a purified matrix including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

An alternative to the preferred method of ECM material isolation comprises rinsing the delaminated biological tissue in saline and soaking it in an antimicrobial agent, for example as disclosed in U.S. Pat. No. 4,956,178. While such techniques can optionally be practiced to isolate ECM material from submucosa, preferred processes avoid the use of antimicrobial agents and the like in a manner which may not only affect the biochemistry of the graft material matrix but also can be undesirably introduced into the tissues of the patient. Other disclosures of methods for the isolation of ECM materials include the preparation of intestinal submucosa described in U.S. Pat. No. 4,902,508, the disclosure of which is incorporated herein by reference. Urinary bladder submucosa and its preparation is described in U.S. Pat. No. 5,554,389, the disclosure of which is incorporated herein by reference. Stomach submucosa has also been obtained and characterized using similar tissue processing techniques, for example as described in U.S. patent application Ser. No. 60/032,683 titled STOMACH SUBMUCOSA DERIVED TISSUE GRAFT, filed on Dec. 10, 1996, which is also incorporated herein by reference in its entirety.

The graft material can be perforated, for example to promote tissue ingrowth and remodeling, for the incorporation of a bioactive material in the graft material, or for the release of a bioactive material through the graft material. In one embodiment, the graft material includes perforations permitting fluid movement through the wall of the medical device. Perforations in the graft material can be sized and configured for a desired application. For example, the perforations can be between about 10 microns to about 100 microns, preferably between about 10 microns and 60 microns, in diameter. The distribution of the perforations can be evenly spaced, such as at least about a 30-60 micron spacing over any suitable portion of the graft material, but preferably over at least about half of the graft material surface. Perforations may be formed in the graft material by any suitable means, including mechanical or laser methods, or a porous graft material can be used. Bioactive material can be placed within or on the porous graft material. Alternatively, bioactive material can elute from a support frame or an underlying graft material, through the porous graft material. The rate at which the bioactive material passes through the porous graft material is determined by several factors, including the size and number of the pores and the size, charge and polarity of the bioactive material molecules.

Optionally, the graft material may be formed as a composite of an extracellular matrix material and other biocompatible fabrics. Accordingly, the graft material may also include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a graft material can be used to make a graft material, provided the final graft material is biocompatible. Polymers that can be formed into a graft material include polyolefins, polyacrylonitrile, nylons, polyaramids and polysulfones, in addition to polyesters, fluorinated polymers, polysiloxanes and polyurethanes as listed above. Preferably the graft material is made of one or more polymers that do not require treatment or modification to be biocompatible. More preferably, the graft material includes a biocompatible polyurethane. Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.).

Attachment of a Support Frame to Graft Materials

The graft material can be attached to the support frame in any suitable manner. For example, the graft material can be welded to the support frame, by the application of localized heat and pressure, or the application of a concentrated solution of graft material which functions as an adhesive. The graft can be attached to the support frame by the use of a small swatch of material placed on the outside of the support frame. A graft material positioned on the luminal or inner surface of the support frame, may be bonded to the material in a variety of ways. Among these are suturing, gluing and heat welding. In the case of a combination of graft material with outer sleeve, these means of attachment may be used as well. In one embodiment, a graft formed as a sleeve can be extended over one or both ends of a tubular support frame to form a "cuff." Cuffs can be sutured to the support frame, sutured from one cuff to the other, or otherwise bonded to the support frame or to another graft positioned on the other side of the support frame. Sutures can also be used to connect the graft material to the support frame. U.S. patent application Ser. No. 11/038,567, filed Jan. 18, 2005 by Lad et al., published as US2005/0159804A1 and incorporated herein by reference, discloses various graft attachment structures suitable for attaching a graft material to a support frame using sutures.

The graft material may be attached to the support frame by any of several design features which may be incorporated into the support frame. The graft material may also be attached to the support frame by providing a porous or perforated support frame or graft material, thus allowing the graft material to act as a forming mandrel for a graft material. By providing the support frame with hooks, or other similar topography, the sleeve may be readily attached to the support frame. The sleeve material may be impaled on such barbs, thus securing the sleeve. With hooks of the appropriate size, the graft material may not be perforated, but rather embedded in the holding topography. Frame structures for attaching a support frame to a graft material described in U.S. patent application Ser. No. 11/056,675, filed Feb. 11, 2005 by Osborne et al., published as US2005/0149167A1 on Jul. 7, 2005 and incorporated herein by reference, are also suitable as a means for attaching the support frame to the graft material.

The graft material can also be precipitated onto the support frame by heating the support frame in a solution of graft material. The graft material can form a matrix on the surface of the support frame, then when properly annealed, the graft material can form a fibular, well organized structure conducive for the attachment and growth of cells. For example, a graft material can be cast inside a support frame in a manner described in U.S. Pat. No. 5,693,085, to Buscemi et al., issued Dec. 2, 1997, which is incorporated herein by reference.

Thus, the graft material may be coated onto the support frame surfaces as desired by spraying or dip coating or electrodeposition or the like or attached in other ways as described above. Such a coating might be about 1-50 microns thick. A graft material coated support frame may also have a graft material over the graft material coating or under the graft material coating. The inside of the support frame may then be coated with graft material. Preferably, in such an arrangement, the sleeve will be SIS. It is also possible in the case of an openwork support frame, to coat the support frame struts with graft material, place a graft material either over or inside the support frame, or both, and then heat bond the sleeve and/or graft material to the coating. This would preferably be done with collagen-based graft material, especially SIS or with fibrin.

In some applications it may be desirable to include perforations in the graft material for fluid movement through the support frame/graft material wall. Such an arrangement is readily obtained as support frames are generally open or perforate with respect to their structure and perforations may be readily formed in a graft material graft material, the perforations extending through the support frame openings. Perforation in graft material graft materials of about 10-60 microns in diameter have been found satisfactory. The distribution of the perforations may be such as to be evenly spaced, such as at 30-60 micron spacing and to occupy about one-half of the graft material surface areas.

Preferably, graft material is oriented on the support frame when the graft material is used in the form of an ECM sheet which is wrapped around the support frame or a tube inserted in the support frame. ECM sheet graft material can be stretched, however its stretchability is predominantly unidirectional. ECM graft material sheet, when used as a sleeve or graft material on a support frame which undergoes expansion and/or contraction, can be attached to the support frame on a "bias," in a manner described in U.S. Pat. No. 5,693,085, to Buscemi et al., issued Dec. 2, 1997, which is incorporated herein by reference. Briefly, the ECM graft material sheet can be oriented at a 45 degree angle relative to the longitudinal axis of a tubular support frame.

Method Embodiments

Still other embodiments provide methods of treating a subject, which can be animal or human, comprising the step of implanting one or more support frames as described herein. Other methods further comprise the step of implanting one or more frames attached to one or more graft members, as described herein. In some embodiments, methods of treating may also include the step of delivering a medical device to a point of treatment in a body vessel, or deploying a medical device at the point of treatment.

Methods of treating peripheral vascular disease, including critical limb ischemia, comprising the endovascular implantation of one or more medical devices are provided. Atherosclerosis underlies most peripheral vascular disease. Narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

The medical device can be implanted in any suitable body vessel. The configuration of the implantable frame can be selected based on the desired site of implantation. For example, for implantation in the superficial artery, popliteal artery or tibial artery, frame designs with increased resistance to crush may be desired. For implantation in the renal or iliac arteries, frame designs with suitable levels of radial force and flexibility may be desired.

In one embodiment, a medical device comprising a balloon-expandable metallic bioabsorbable frame portion and an attached graft material can be endolumenally delivered to a point of treatment within an infrapopliteal artery, such as the tibial or peroneal artery, to treat CLI. For treating focal disease conditions, balloon expandable medical devices can comprise an expandable frame attached to a coating that encloses and is attached to the frame. The frame can be formed from a metallic bioabsorbable material, or comprise a coating of a metallic bioabsorbable material over at least a portion of the frame. The frame can be configured to include a barb or other means of securing the medical device to the wall of a body vessel upon implantation.

In another embodiment, a medical device can be configured as a self-expanding device configured to provide a desirable amount of outward radial force to secure the medical device within the body vessel. The medical device can be preferably implanted within the tibial arteries for treatment of CLI. For instance, the medical device can be configured as a vascular stent having a self-expanding support frame formed from a superelastic self-expanding nickel-titanium alloy coated with a metallic bioabsorbable material and attached to a graft material. The use of a self-expanding frame can be preferably used when the body vessel to be stented extends into the distal popliteal segment. The selection of the type of implantable frame can also be informed by the possibility of external compression of an implant site within a body vessel during flexion of the leg.

Methods for delivering a medical device as described herein to any suitable body vessel are also provided, such as a vein, artery, biliary duct, ureteral vessel, body passage or portion of the alimentary canal.

While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

While many preferred embodiments discussed herein include a graft with a stent or other support frame, other embodiments employ a support frame comprising certain forms of metallic bioabsorbable material as disclosed herein in applications which do not necessarily involve a graft.

The invention includes other embodiments within the scope of the claims, and variations of all embodiments.

We claim:

1. A medical device for implantation in a body vessel comprising:
   a support frame comprising a core material selected from the group consisting of stainless steel, a cobalt-chromium alloy and a nickel-titanium alloy and a bioabsorbable alloy comprising a first and a second metallic material, where the core material is at least partially enclosed by the bioabsorbable alloy, and a graft material, where the support frame attaches to the graft material defining a tubular lumen, where the graft material comprises an extracellular matrix material and where the extracellular matrix material is a remodelable material that induces cellular infiltration and neovascularization.

2. The medical device of claim 1, wherein the bioabsorbable alloy comprises a material selected from a first group consisting of: magnesium, titanium, zirconium, niobium, tantalum, zinc, and silicon.

3. The medical device of claim 2, where the bioabsorbable alloy comprises magnesium and about 0.1% to about 2% aluminum.

4. The medical device of claim 3, where the bioabsorbable alloy further comprises up to about 1% of a rare earth metal.

5. The medical device of claim 1, wherein the bioabsorbable alloy comprises magnesium and one or more metals.

6. The medical device of claim 5, wherein the bioabsorbable alloy comprises a first metal selected from a first group consisting of: magnesium, titanium, zirconium, niobium, tantalum, zinc, and silicon; and a second metal selected from the group consisting of: lithium, sodium, potassium, calcium, iron, and manganese.

7. The medical device of claim 5, wherein the bioabsorbable alloy is selected from the group consisting of: lithium-magnesium, sodium-magnesium, and zinc-titanium.

8. The medical device of claim 5, wherein the bioabsorbable alloy further comprises gold.

9. The medical device of claim 1, where the bioabsorbable alloy comprises at least 90% magnesium.

10. The medical device of claim 9, where the bioabsorbable alloy further comprises between about 3.7% and 5.5% yttrium.

11. The medical device of claim 10, where the bioabsorbable alloy further comprises between about 1.5% and 4.4% rare earth materials.

12. The medical device of claim 1, where the bioabsorbable alloy consists of 0.7-4.3% yttrium, 2.4-4.4% rare earth metals, at least 0.4% zirconium and magnesium, the rare earth metals comprising 2.0-2.5% neodymium.

13. The medical device of claim 1, where the support frame is moveable from a radially compressed configuration to a radially expanded configuration, the medical device having a diameter in the radially expanded state of at least about 4 mm.

14. The medical device of claim 1, where the support frame has an elastic recoil of about 1-10%.

15. The medical device of claim 1, where the extracellular matrix material is submucosa.

16. The medical device of claim 1, where the graft material has a perforated region defining a plurality of holes sized between about 10 microns and 100 microns.

17. The medical device of claim 1, where the bioabsorbable alloy comprises magnesium and one or more metals selected from the group consisting of: titanium, zirconium, niobium, tantalum, zinc, yttrium, and silicon; and further comprises at least one metal selected from the group consisting of: aluminum, lithium, sodium, potassium, calcium, iron, gold, manganese, lanthanum, cerium, praseodymium, neodymium, promethium, samarium, europium, gadolinium, terbium, dysprosium, holmium, erbium, thulium, ytterbium, and lutetium; where the support frame has an elastic recoil of about 1-10%; and where the graft material comprises an extracellular matrix material and a bioactive agent.

18. The medical device of claim 1, where the extracellular matrix material comprises perforations.

* * * * *